(12) United States Patent
Crossgrove et al.

(10) Patent No.: US 11,129,655 B2
(45) Date of Patent: Sep. 28, 2021

(54) SYSTEM AND METHOD FOR BONE FUSING IMPLANTS

(71) Applicant: SPINEFRONTIER, INC, Malden, MA (US)

(72) Inventors: Jeremy Crossgrove, Brookline, MA (US); Oscar Herrera, Malden, MA (US); Michael Emery, Windham, NH (US); Joshua Finkel, Malden, MA (US); Kyle Woodard, Malden, MA (US); Kingsley R. Chin, Wilton Manors, FL (US)

(73) Assignee: KIC VENTURES, LLC, Malden, MA (US)

( * ) Notice: Subject to any disclaimer, the term of this patent is extended or adjusted under 35 U.S.C. 154(b) by 221 days.

(21) Appl. No.: 16/515,477

(22) Filed: Jul. 18, 2019

(65) Prior Publication Data
US 2020/0022817 A1 Jan. 23, 2020

Related U.S. Application Data

(60) Provisional application No. 62/701,229, filed on Jul. 20, 2018.

(51) Int. Cl.
*A61B 17/86* (2006.01)
*A61F 2/30* (2006.01)

(52) U.S. Cl.
CPC .......... *A61B 17/863* (2013.01); *A61B 17/864* (2013.01); *A61B 17/866* (2013.01); *A61F 2/30988* (2013.01); *A61F 2002/30622* (2013.01); *A61F 2002/30769* (2013.01);
(Continued)

(58) Field of Classification Search
CPC ... A61B 17/864; A61B 17/863; A61B 17/866; A61F 2002/30622
See application file for complete search history.

(56) References Cited

U.S. PATENT DOCUMENTS

| 8,388,667 B2 | 3/2013 | Reiley et al. |
| 8,562,651 B2 | 10/2013 | Metcalf et al. |
| 8,579,947 B2 | 11/2013 | Wu |

(Continued)

OTHER PUBLICATIONS

PCT/ISR; Sep. 27, 2019.

*Primary Examiner* — Christian A Sevilla
(74) *Attorney, Agent, or Firm* — AKC Patents, LLC; Aliki K. Collins

(57) ABSTRACT

A bone fusing implant device includes an elongated body extending along a longitudinal direction. The elongated body includes a first segment having an outer surface with cortical threads, a second segment having an outer surface with cancellous threads, a top segment and a bottom segment. The first segment is adjacent to the second segment along the longitudinal direction and is configured to engage a cortical bone with the cortical threads and the second segment is configured to engage a cancellous bone with the cancellous threads. The elongated body has one or more elongated fusing gutters extending along the longitudinal direction on an outer surface of the elongated body covering the first and second segments, a central opening extending along the longitudinal direction through the elongated body's center and one or more through-openings that extend horizontally and intersect with the one or more fusing gutters.

12 Claims, 9 Drawing Sheets

(52) U.S. Cl.
CPC ............... *A61F 2002/30782* (2013.01); *A61F 2002/30995* (2013.01)

(56) References Cited

U.S. PATENT DOCUMENTS

| | | |
|---|---|---|
| 8,808,377 B2 | 8/2014 | Donner |
| 9,044,321 B2 | 6/2015 | Mauldin et al. |
| 9,486,264 B2 | 11/2016 | Reiley et al. |
| 9,492,201 B2 | 11/2016 | Reiley |
| 9,492,284 B2 | 11/2016 | Ginn et al. |
| 9,662,128 B2 | 5/2017 | Reiley |
| 9,662,158 B2 | 5/2017 | Reiley |
| 9,687,285 B2 | 6/2017 | Robinson |
| 9,717,538 B2 | 8/2017 | Chin et al. |
| 9,737,312 B2 | 8/2017 | Huwais |
| 9,737,414 B2 | 8/2017 | Felt et al. |
| 2009/0198291 A1* | 8/2009 | Kevin ............... A61B 17/863 606/305 |
| 2009/0264937 A1* | 10/2009 | Parrott ............... A61B 17/8625 606/305 |
| 2011/0060373 A1* | 3/2011 | Russell ............... A61B 17/8057 606/304 |
| 2012/0089195 A1* | 4/2012 | Yedlicka ............ A61B 17/8635 606/304 |
| 2015/0080972 A1* | 3/2015 | Chin .................... A61B 17/863 606/304 |
| 2018/0042652 A1* | 2/2018 | Mari .................. A61B 17/8685 |

\* cited by examiner

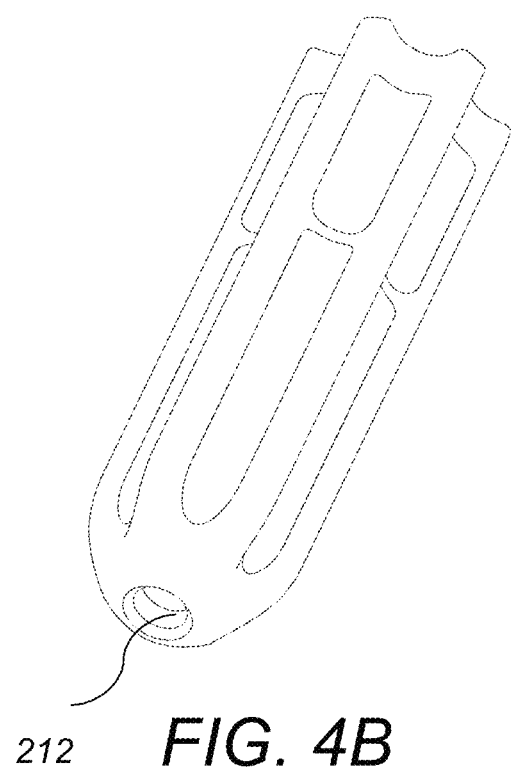
*FIG. 4B*  212
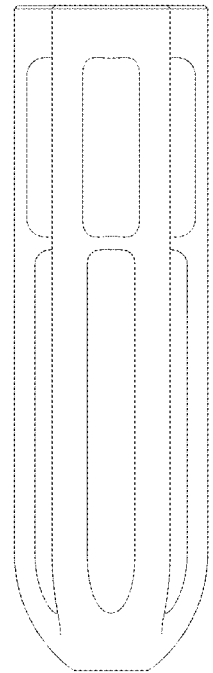
*FIG. 4C*
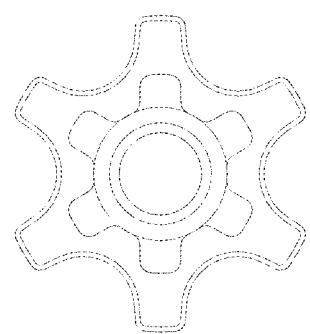
*FIG. 4D*
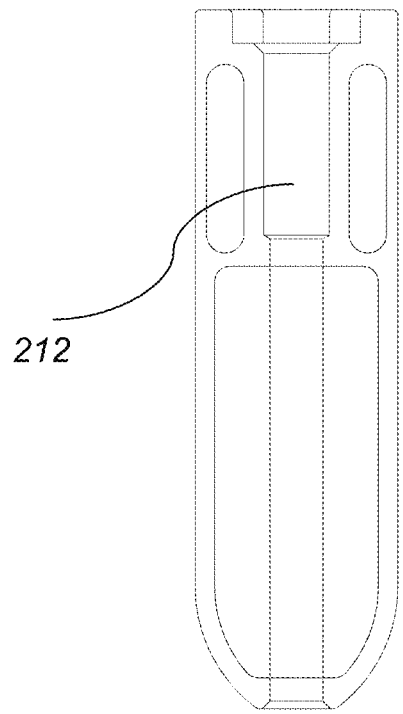
212  *FIG. 4E*

SYSTEM AND METHOD FOR BONE FUSING IMPLANTS

CROSS REFERENCE TO RELATED CO-PENDING APPLICATIONS

This application claims the benefit of U.S. provisional application Ser. No. 62/701,229 filed Jul. 20, 2018 and entitled "SYSTEM AND METHOD FOR BONE FUSING IMPLANTS", the contents of which are expressly incorporated herein by reference.

FIELD OF THE INVENTION

The present invention relates to a system and a method for bone fusing implants, and more particularly to bone fusing implants that are used for sacroiliac joint fusion.

BACKGROUND OF THE INVENTION

The human spine includes individual vertebras that are connected to each other. Under normal circumstances the structures that make up the spine function are configured to protect the neural structures, allow us to stand erect, bear axial loads, and are flexible for bending and rotation. Disorders of the spine occur when one or more of these spine structures are abnormal. In these pathologic circumstances, surgery may be tried to restore the spine to the normal state and to relieve the patient of pain. Spine surgery for a multitude of spinal disorders is often used for filling voids within a pathologic vertebral body (exemplified by kyphoplasty or vertebroplasty procedures), replacement of a degenerated intervertebral disc with an intervertebral implant device that preserves mobility (disc replacement) or for fusing adjacent vertebral segments (interbody and posterolateral fusions). Fusion works well because it stops pain due to movement at the joints, holds the spine in place after correcting a deformity, and prevents instability and or deformity of the spine after spine procedures such as laminectomies or verterbrectomies.

One area where fusion is applicable is for sacroiliac joint fusion (SIJF). The sacroiliac joint (SIJ) is a firm, small joint that lies at the junction of the sacrum and the pelvis. While most of the vertebras of the spine are mobile, the sacrum is made up of five vertebras that are fused together and do not move. The iliac bones are the two large bones that make up the pelvis. The sacroiliac joints connect the spine to the pelvis. The sacrum and the iliac bones are held together by a collection of strong ligaments. These joints are important in transferring the load of the upper body to the lower body, supporting the entire weight of the upper body when we are erect, which in turn results in stress to this weight-bearing area of the pelvis and spine. Pathologies of the SIJ include degenerative sacroiliitis (arthritis), sacroiliac disruption, tumors and other type of injuries. Sacroiliac joint (SI) fusion is used for treating degenerative sacroiliitis, sacroiliac disruption, and for stabilizing the SI joint after sacrectomy or after injury.

There is increasing concensus among surgeons that there is a need to develop devices, instruments, and methods to limit the size of the incision, extensive muscle stripping, prolonged retraction of muscles for visualization, avoidance of neural tissue retraction and injury, and denervation and devascularization that are known to contribute to poorer patient outcome after traditional open surgeries to treat pathologies deep within the body. In many cases these complications lead to permanent scarring and pain that can be more severe than the pain from the initial ailment. Limiting these complications in addition to the operative, general anesthesia, and recovery times are among the goals of this invention and that of percutaneous or minimally invasive surgeries.

This invention addresses the need for bone fusing implants that are used for sacroiliac joint fusion and for implant insertion tools that adhere to the principals of the less exposure surgery (LES) of outpatient surgery, which include minimizing the size of the incision, minimizing extensive muscle stripping, minimizing prolonged retraction of muscles for visualization, and preventing neural tissue retraction and injury.

SUMMARY OF THE INVENTION

The present invention relates to a system and a method for bone fusing implants, and more particularly to bone fusing implants that are used for sacroiliac joint fusion.

In general, in one aspect, the invention features a bone fusing implant device including an elongated body extending along a longitudinal direction. The elongated body includes a first segment having an outer surface with cortical threads, a second segment having an outer surface with cancellous threads, a top segment and a bottom segment. The first segment is adjacent to the second segment along the longitudinal direction and is configured to engage a cortical bone with the cortical threads and the second segment is configured to engage a cancellous bone with the cancellous threads. The elongated body has one or more elongated fusing gutters extending along the longitudinal direction on an outer surface of the elongated body covering the first and second segments, a central opening extending along the longitudinal direction through the elongated body's center and one or more through-openings that extend horizontally and intersect with the one or more fusing gutters.

Implementations of this aspect of the invention may include one or more of the following features. The top segment is tapered and adjacent to the first segment along the longitudinal direction and has an outer surface with cortical threads that are thicker than the cortical threads of the first segment. The bottom segment is tapered and adjacent to the second segment along the longitudinal direction and has a self-cutting tip. The central opening includes a top portion and a bottom portion and the bottom portion has a smaller diameter than the top portion. The one or more through-openings that extend horizontally intersect with the top portion of the central opening and allow the one or more fusing gutters to communicate with the central opening. The elongated fusing gutters are arranged 120 degrees apart from each other around the elongated body and cut through the cortical threads and the cancellous threads. The first segment has a length equal to the cortical bone's length and the second segment has a length equal to the cancellous bone's length. The device further includes bone material inserted into the top portion of the central opening and funneled outwardly through the one or more horizontally extending openings into the one or more elongated fusing gutters. The elongated fusing gutters comprise a trabecular lattice structure, and do not cut through the cortical threads and the cancellous threads. The bone material may be bone graft, bone putty, stem cells, autograft bone, or allograft bone. The elongated body is made of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made.

In general, in another aspect, the invention features a bone fusing implant device including an elongated body extending along a longitudinal direction and having a star-shaped cross-section. The elongated body includes a central through-opening extending through the elongated body's center along the longitudinal direction and an outer surface with alternating elongated ridges and slit openings extending along the longitudinal direction. The outer surface is coated with bone growth enhancing additives.

In general, in another aspect, the invention features a method for bone fusing including the following. First, providing an implant device comprising an elongated body extending along a longitudinal direction. The elongated body includes a first segment having an outer surface with cortical threads, a second segment having an outer surface with cancellous threads, a top segment and a bottom segment. The first segment is adjacent to the second segment along the longitudinal direction. Next, engaging a cortical bone with the cortical threads of the first segment. Next, engaging a cancellous bone with the cancellous threads of the second segment. The elongated body includes one or more elongated fusing gutters extending along the longitudinal direction on an outer surface of the elongated body covering the first and second segments, a central opening extending along the longitudinal direction through the elongated body's center and one or more through-openings that extend horizontally and intersect with the one or more fusing gutters. The method further includes inserting bone material into a top portion of the central opening and funneling the bone material outwardly through the one or more horizontally extending openings into the one or more elongated fusing gutters.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views:

FIG. 4B is a bottom perspective view of the bone fusing peg implant of FIG. 4A;

FIG. 4C is a side view of the bone fusing peg implant of FIG. 4A;

FIG. 4D is a top view of the bone fusing peg implant of FIG. 4A;

FIG. 4E is a cross-sectional view of the bone fusing peg implant of FIG. 4A along plane A-A';

DETAILED DESCRIPTION OF THE INVENTION

The present invention relates to a system and a method for bone fusing implants, and more particularly to bone fusing implants that are used for sacroiliac (SI) joint fusion.

Figure 1A:
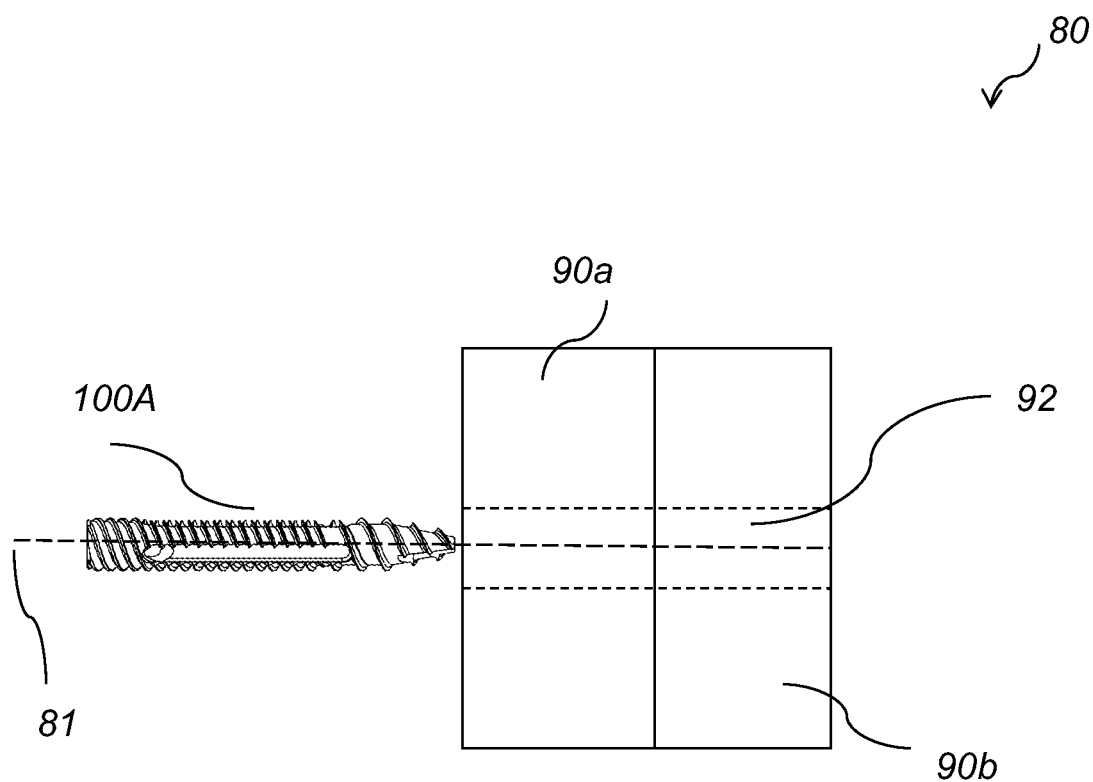
FIG. 1A is a schematic side view of an embodiment of a bone fusing implant that is used for fusing two adjacent bones, according to this invention.
Figure 1B:
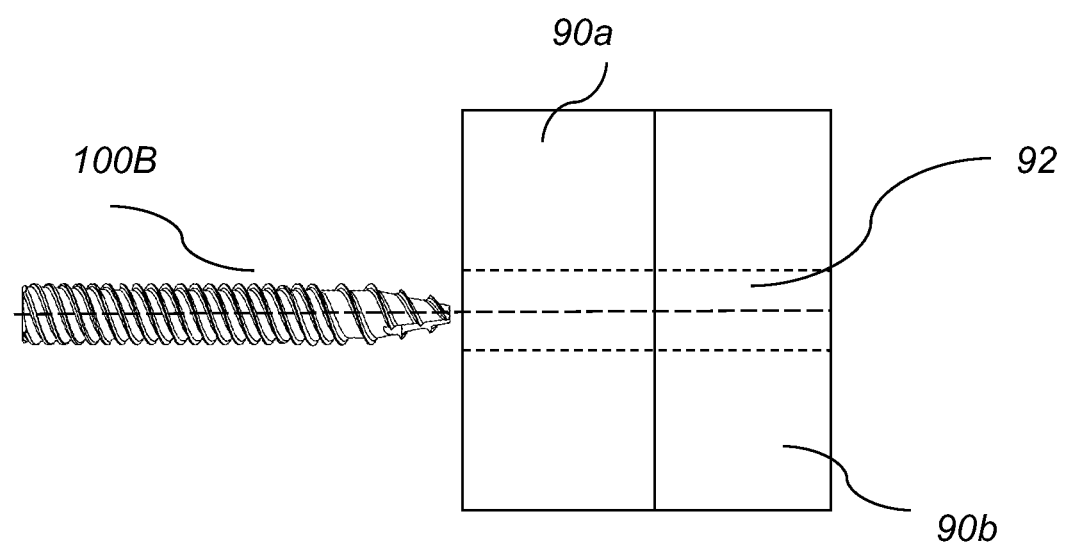
FIG. 1B is a schematic side view of another embodiment of a bone fusing implant that is used for fusing two adjacent bones, according to this invention.

Referring to FIG. 1A, FIG. 1B, FIG. 6A-FIG. 6C, in SIJF surgery one or more openings 92 are formed along the arrow direction 81 and bone fusing implants 100A, 100B, or 200 are inserted in the formed openings 92. Referring to FIG. 1A, bone fusing implant 100A is inserted in opening 92 that is formed through two stacked adjacent bone members 90a and 90b. In one example, bone member 90a is primarily a cortical (compact) bone and bone member 90b is in majority a cancellous (porous) bone.

Figure 2A:
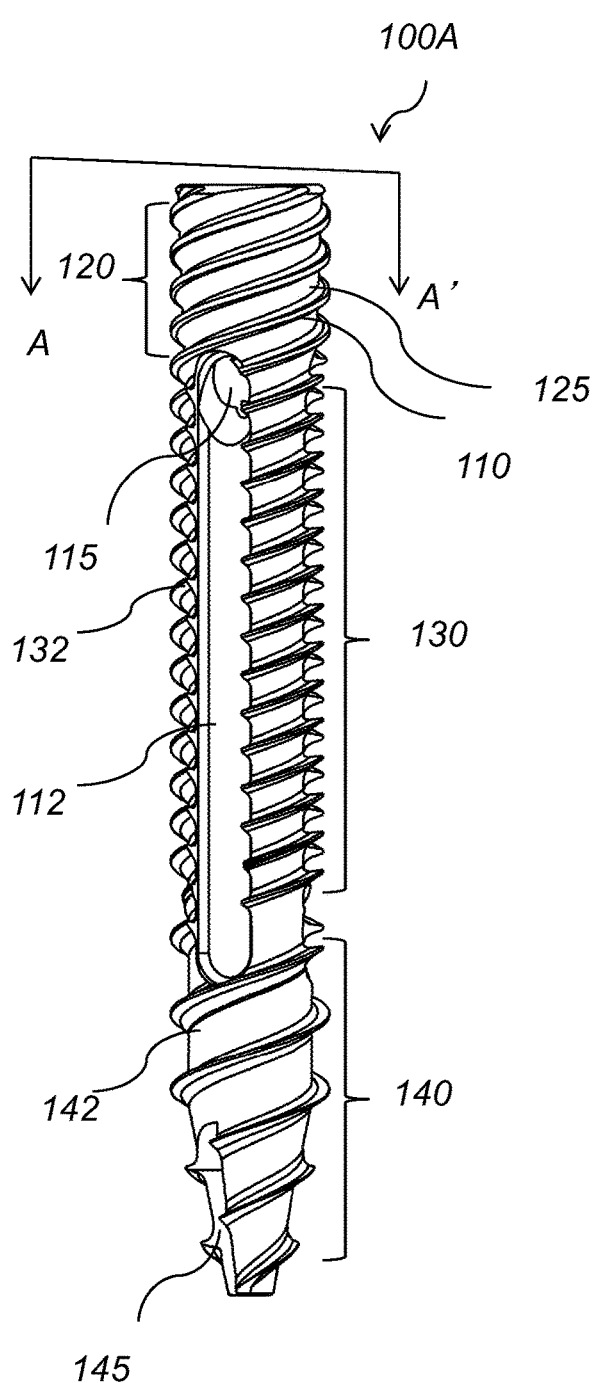
FIG. 2A is a perspective view of the bone fusing implant of FIG. 1A.
Figure 2B:
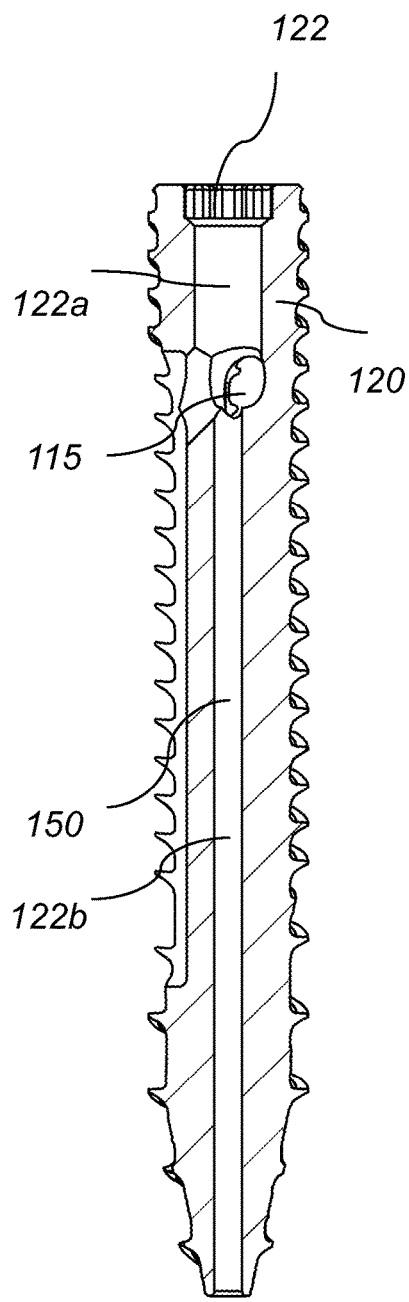
FIG. 2B is a cross-sectional view of the bone fusing implant of FIG. 2A along plane A-A'.
Figures 3A, 3B:
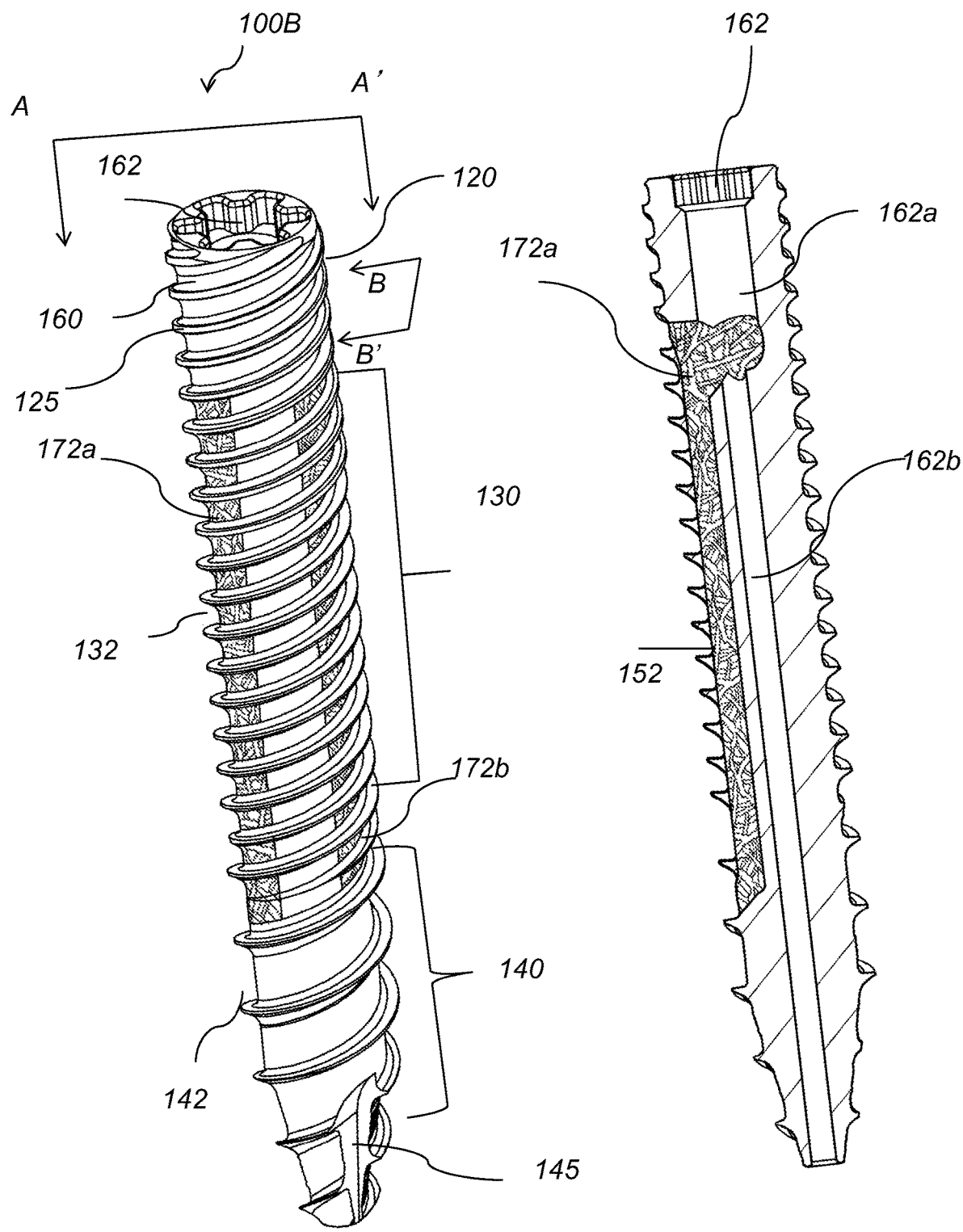
FIG. 3A is a perspective view of the bone fusing implant of FIG. 1B.
FIG. 3B is a cross-sectional view of the bone fusing implant of FIG. 3A along plane A-A'.
Figure 3C:
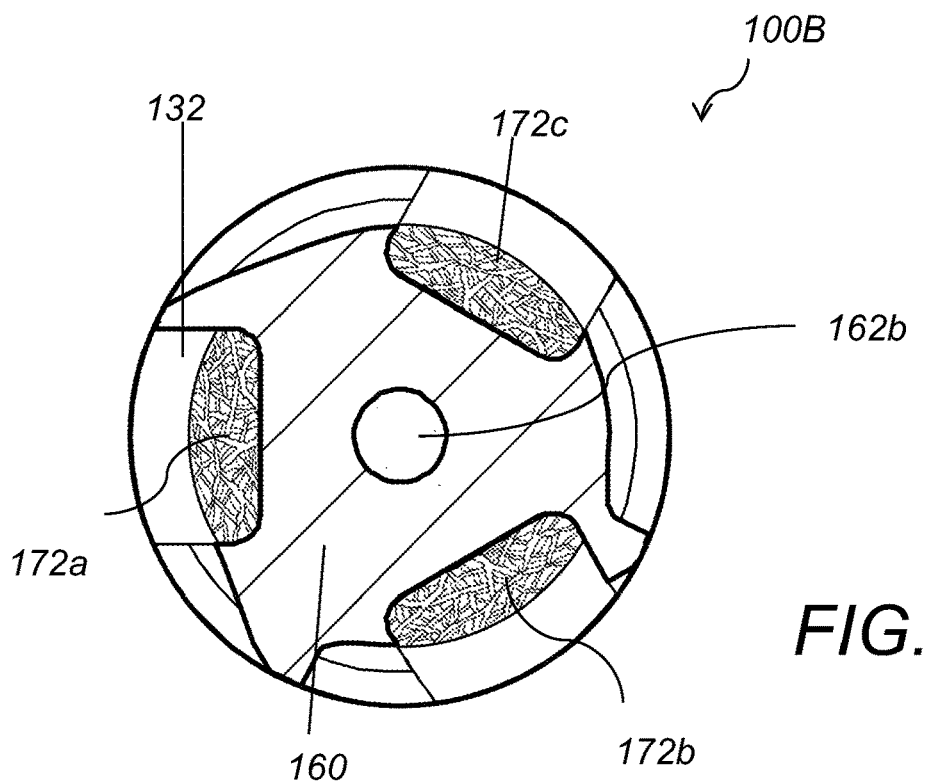
FIG. 3C is a cross-sectional view of the bone fusing implant of FIG. 3A along plane B-B'.
Figure 3D:
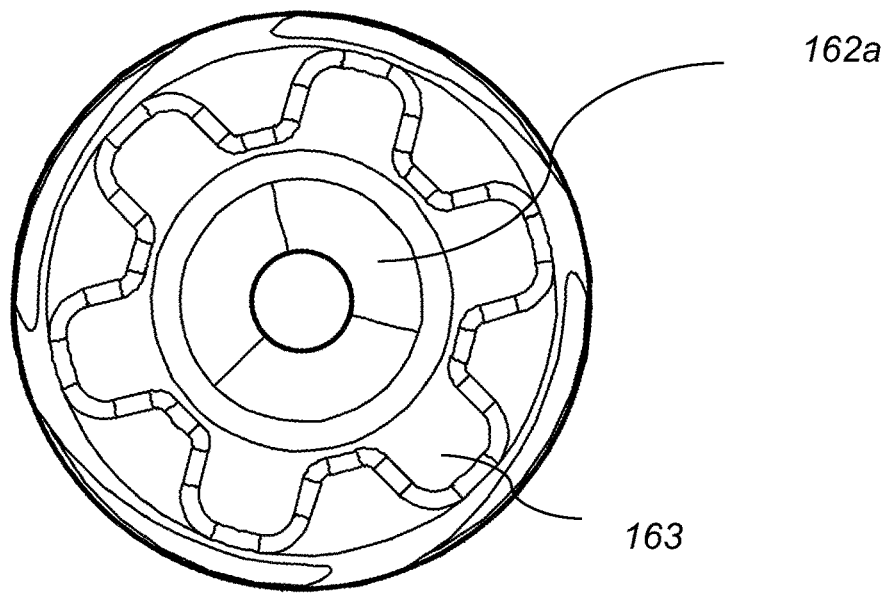
FIG. 3D is a top view of the bone fusing implant of FIG. 3A.

Referring to FIG. 2A and FIG. 2B, bone fusing implant 100A includes a cylindrical hollow threaded body 110 that has three elongated slit openings 112 (fusion gutters), a central through opening 122 that extends the entire length of the implant, horizontally extending through-openings 115, a first segment 130 with cortical threads 132, a second segment 140 with cancellous threads 142, a top segment 120 that is tapered and has threads 125 that are thicker than the cortical threads 132, and bottom tip segment 145 that is tapered and self-cutting. Cortical threads 132 are closely spaced. Screws with cortical threads are used for fixation of cortical (compact) bone. Cancellous threads 142 are widely spaced. Screws with cancellous threads are designed for fixation of cancellous (porous) bone. Since cancellous bone is much less dense than cortical bone, the screw threads are spaced further apart, leaving space for more bone in between each thread. In one example, implant 100A has a length of 35 mm and a diameter of 12 mm. The segment 130 with the cortical threads 132 has a length of 15 mm, which corresponds to the width of the cortical bone 90a. The segment 140 with the cancellous threads 142 has a length of 20 mm, which corresponds to the width of the cancellous bone 90b. Slit openings 112 are arranged 120 degrees apart and cut through the screw threads 132, and intersect at the top end with the horizontally extending through-opening 115. Central opening 122 includes a top portion 122a and a lower portion 122b and the lower portion 122b has a smaller diameter than the top portion 122a. The horizontally extending through-openings 115 intersect with the top portion 122a of the central through opening 122 and allows slit openings 112 to communicate with the through-opening 122.

The top portion 122a of the through-opening 122 is used for inserting bone material, such as bone graft, bone putty, stem cells, autograft, and allograft, among others, into the central through-opening 122 and then funneling the bone material outward through the three horizontal through-openings 115 along the three slit openings (fusion channels) 112 to aid fusion across the SI joint. In other examples, bone implant 100A, has a length of 60 mm and includes a slit opening 112 that has a length of 23.1 mm. Bone implant 100A is made of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man made.

Referring to FIG. 3A-FIG. 3D, in another embodiment, bone implant 100B includes a cylindrical hollow threaded body 160 that has a central through opening 162 that extends the entire length of the implant, a first segment 130 with cortical threads 132 and a second segment 140 with cancellous threads 142. Body 160 also includes a top segment 120 that is tapered and has threads 125 that are thicker than the cortical threads 132, and a bottom tip segment 145 that is tapered and self-cutting. The tapering of the top segment portion 120 refers to the minor diameter of the screw tapering up(growing) as it gets closer to the proximal end. This tapering causes compression via an increasing interference between the screw and the pilot-hole. Central opening 162 includes a top portion 162a and a lower portion 162b and the lower portion 162b has a smaller diameter than the top portion 162a. In this embodiment, the cylindrical body includes three slit openings 172a, 172b, 172c (trabecular gutters) that are arranged 120 degrees apart. Slit openings 172a, 172b, 172c do not cut through the outer threads 132 and 142 and communicate at the top end with the top portion 162a of the central through opening 162. Slit openings 172a, 172b, 172c includes a trabecular (lattice) structure 152 and may be filled with bone growth medium. The bone growth medium may be bone, putty, stem cells, or bone graft, among others. The bone graft medium may be inserted via the central opening 162, or the slit openings 172a, 172b, 172c either before or after implantation. The top surface of the elongated body includes a six-lobe shaped structure 163 that is used for receiving a driver tool. Bone implant 100B is manufactured using "additive manufacturing" techniques, such as electron beam melting (EBM), and direct metal laser sintering (DMLS), among others.

Figure 4A:
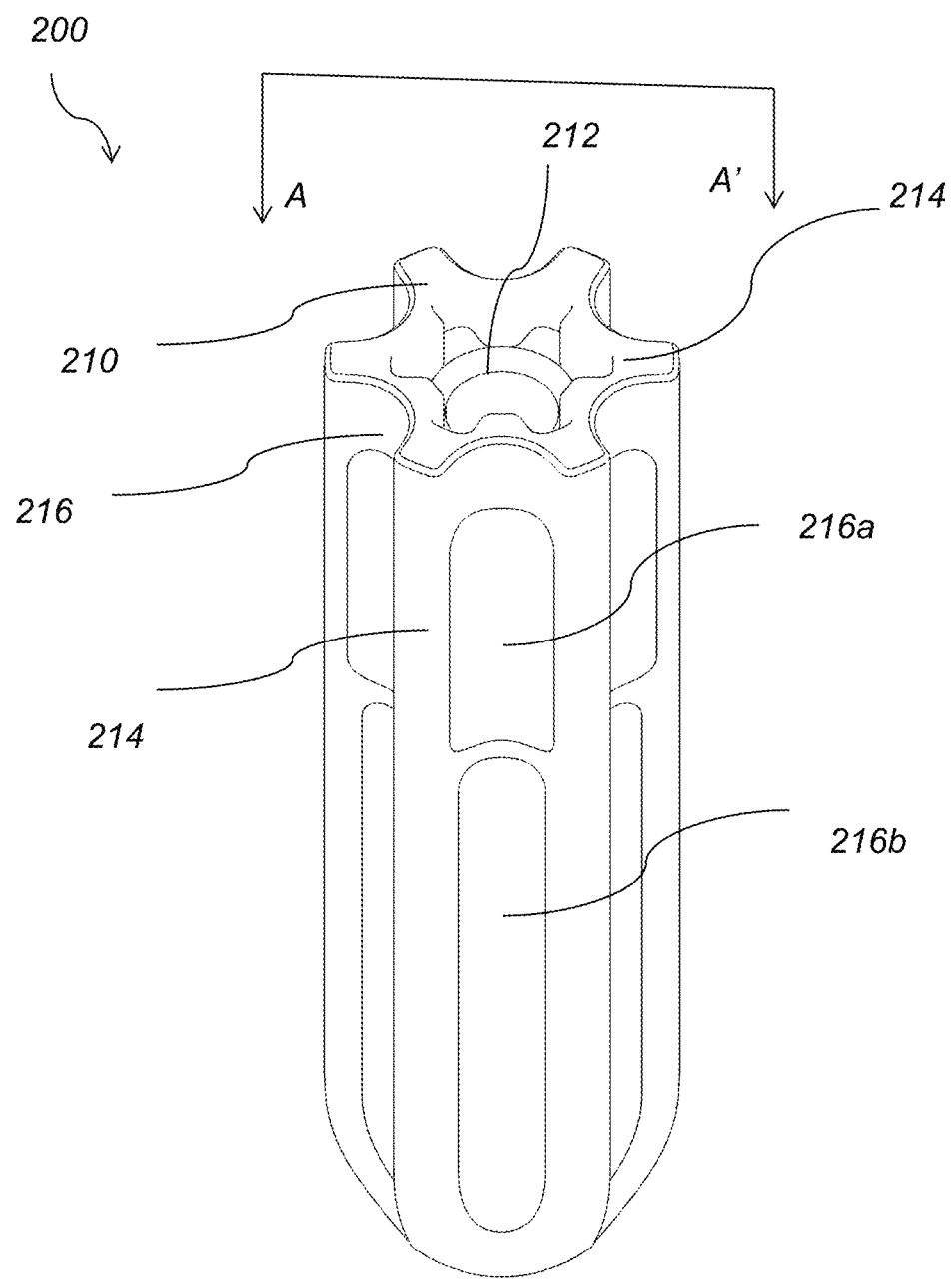
FIG. 4A is a top perspective view of a bone fusing peg implant, according to this invention.
Figure 5A:
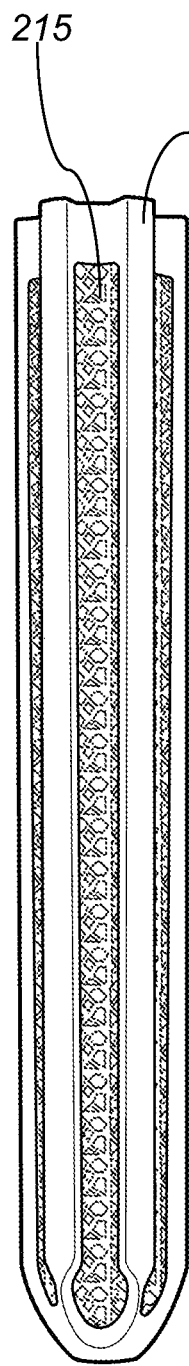
FIG. 5A-FIG. 5C depict side views of other embodiments of the bone fusing peg implant.
Figure 5B:
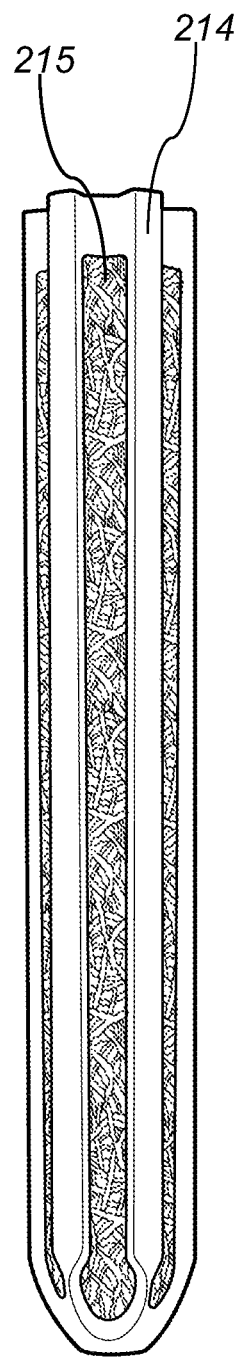
Figure 5C:
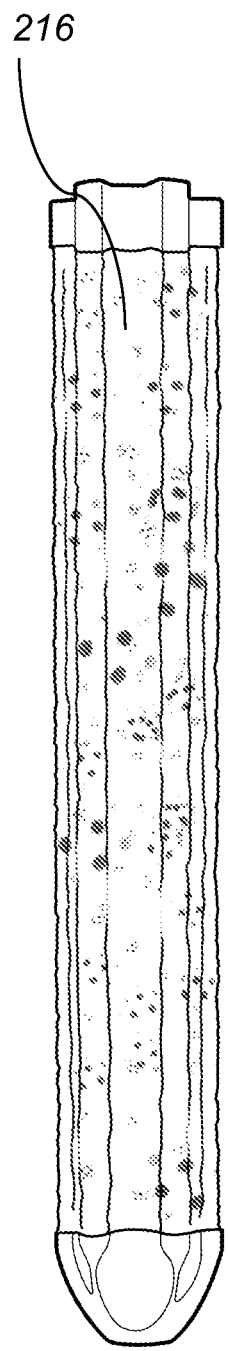

Referring to FIG. 4A-FIG. 4E, in another embodiment, bone fusing implant 200 includes a star-shaped hollow elongated body 210 that has a central through opening 212, outer ridges 214 and slit openings 216a, 216b. The star-shaped elongated body 210 has increased outer surface area due to the surface areas provided by ridges 214, shown in FIG. 4A and FIG. 5A and FIG. 5B. The increased outer surface area contributes to better joint fixation by minimizing micro-motion and therefore improving bone fusion. In one example, implant 200 has a length of 45 mm, a diameter of 15.5 mm and is made of a titanium rod. The outer surface 216 of the implant 200 may be coated with bone growth enhancing additives such as calcium phosphates, hydroxyapatite, or similar, which provides a textured porous surface 216, as shown in FIG. 4A and FIG. 5C. The implant 200 is coated via plasma evaporation, sputtering or electron beam melting. Sections 216a and 216b of the implant 200 may be additively manufactured to form a trabecular or lattice structure 215, as shown in FIG. 5A and FIG. 5B. In another embodiment, implant 200 does not have any slit openings 216a, 216b or other internal cavities, as shown in FIG. 5C.

Figure 6A:
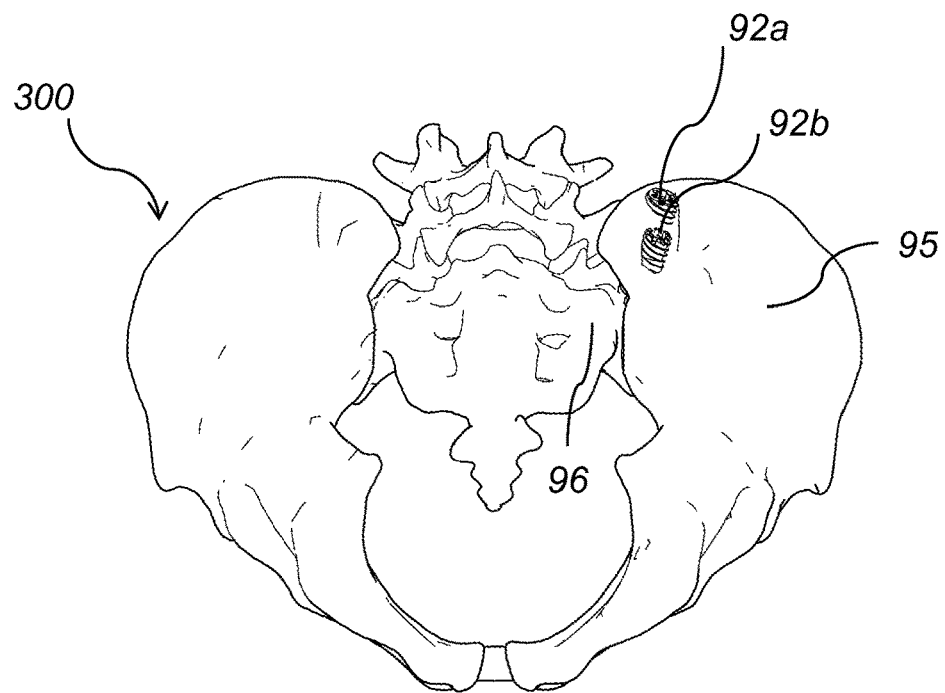
FIG. 6A is a schematic posterior view of the pelvic bones and sacrum held together by two inserted bone fusing implants.
Figure 6B:
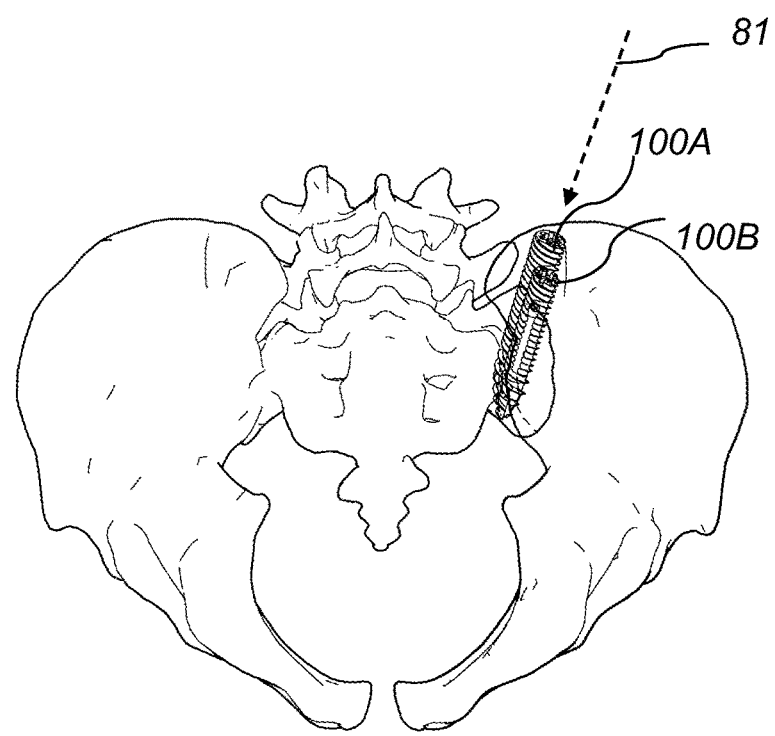
FIG. 6B is a schematic posterior view of the pelvic bones and sacrum indicating the two bone fusing implants as they are being inserted.
Figure 6C:
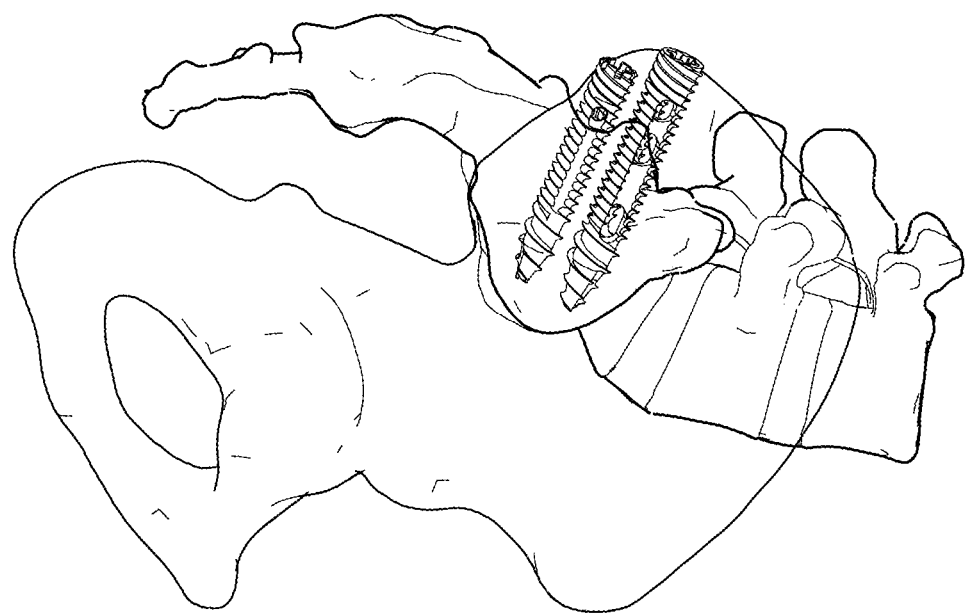
FIG. 6C is a schematic side view of the pelvic bones and sacrum indicating the two bone fusing implants as they are being inserted.
Figure 7:
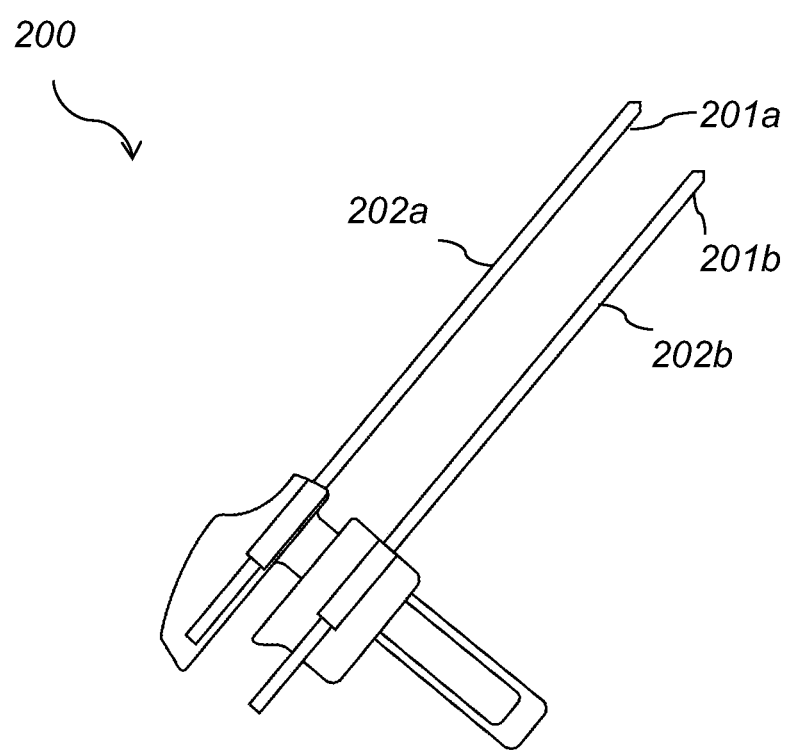
FIG. 7 depicts a pin guide tool.

Bone fusing implants 100A or 100B or 200 are inserted into openings formed through the ilium 95 and the adjacent sacrum 96. Referring to FIG. 6A-FIG. 6C, openings 92a, 92b are formed through the ilium 95 and the adjacent sacrum 96 (or through stacked adjacent bones 90a, 90b) by inserting pins 202a, 202b via a pin guide tool 200, shown in FIG. 7 and described in U.S. Pat. No. 9,717,538, the contents of which are incorporated herewith by reference. The relative position, distance, pin depth and orientation of pins 202a, 202b is set by the pin guide 200. After the insertion of pins 202a, 202b, the openings 92a, 92b are dilated with a dilator. An example of a dilator is also shown and described in U.S. Pat. No. 971,753. Next, a tissue protector is inserted over the dilator and the dilator is removed leaving the pin 202a or 202b in place to form an opening to the ilium. Next, a cannulated drill is passed through the tissue protector over each of the pins and drilled into the ilium to a desired depth. Next, for implants 100A, 100B, a tap is used to tap threads in the formed opening 92a prior to inserting implants. For implant 200, a broach 300 is impacted into the bone to generate the opening pattern of implant 200. Next, the bone fusing implants 100A, 100B, or 200 are inserted into the corresponding formed openings 92a, 92b and the pin guides are removed. The steps are repeated for inserting pins for another implant.

Several embodiments of the present invention have been described. Nevertheless, it will be understood that various modifications may be made without departing from the spirit and scope of the invention. Accordingly, other embodiments are within the scope of the following claims.

What is claimed is:

1. A bone fusing implant device comprising:
an elongated body extending along a longitudinal direction;
wherein the elongated body comprises a first segment having an outer surface with cortical threads, a second segment having an outer surface with cancellous threads, a top segment and a bottom segment;
wherein the first segment is adjacent to the second segment along the longitudinal direction and is configured to engage a cortical hone with the cortical threads and the second segment is configured to engage a cancellous bone with the cancellous threads;
wherein the elongated body comprises one or more elongated fusing gutters extending along the longitudinal direction on an outer surface of the elongated body covering the first and second segments, a central opening extending along the longitudinal direction through the elongated body's center and one or more through-openings that extend horizontally and intersect with the one or more fusing gutters;
wherein the cortical threads are more closely spaced than the cancellous threads.

2. The device of claim 1, wherein the top segment is tapered and adjacent to the first segment along the longitudinal direction and comprises an outer surface with cortical threads that are thicker than the cortical threads of the first segment, and wherein the bottom segment is tapered and adjacent to the second segment along the longitudinal direction and comprises a self-cutting tip.

3. The device of claim 1, wherein the central opening comprises a top portion and a bottom portion and wherein the bottom portion comprises a smaller diameter than the top portion.

4. The device of claim 3, wherein the one or more through-openings that extend horizontally intersect with the top portion of the central opening and allow the one or more fusing gutters to communicate with the central opening.

5. The device of claim 1, wherein the elongated fusing gutters are arranged 120 degrees apart from each other around the elongated body and cut through the cortical threads and the cancellous threads.

6. The device of claim 1, wherein the first segment has a length equal to the cortical bone's length and the second segment has a length equal to the cancellous bone's length.

7. The device of claim 3, further comprising bone material inserted into the top portion of the central opening and funneled outwardly through the one or more horizontally extending openings into the one or more elongated fusing gutters.

8. The device of claim 1, wherein the elongated fusing gutters comprise a trabecular lattice structure, and do not cut through the cortical threads and the cancellous threads.

9. The device of claim 7, wherein the bone material comprises one of bone graft, bone putty, stem cells, autograft bone, or allograft bone.

10. The device of claim 1, wherein the elongated body comprises one of bone, polyetheretherketone (PEEK), Nitinol, metals, titanium, steel, metal composites, biodegradable materials, collagen matrices, synthetic polymers, polysaccharides, calcium minerals, calcium salts, or composites containing calcium or phosphorous naturally or man-made.

11. A method for bone fusing comprising:
  providing an implant device comprising an elongated body extending along a longitudinal direction, wherein the elongated body comprises a first segment having an outer surface with cortical threads, a second segment having an outer surface with cancellous threads, a top segment and a bottom segment, and wherein the first segment is adjacent to the second segment along the longitudinal direction;
  engaging a cortical bone with the cortical threads of the first segment;
  engaging a cancellous bone with the cancellous threads of the second segment;
  wherein the elongated body comprises one or more elongated fusing gutters extending along the longitudinal direction on an outer surface of the elongated body covering the first and second segments, a central opening extending along the longitudinal direction through the elongated body's center and one or more through-openings that extend horizontally and intersect with the one or more fusing gutters;
  wherein the cortical threads are more closely spaced than the cancellous threads.

12. The method of claim 11, further comprising inserting bone material into a top portion of the central opening and funneling the bone material outwardly through the one or more horizontally extending openings into the one or more elongated fusing gutters.

* * * * *